United States Patent [19]

Westberg et al.

[11] 4,249,226
[45] Feb. 3, 1981

[54] GROUNDING STRAP

[75] Inventors: Walter M. Westberg; Daniel J. Newes, both of St. Paul, Minn.

[73] Assignee: Minnesota Mining and Manufacturing Company, St. Paul, Minn.

[21] Appl. No.: 13,813

[22] Filed: Feb. 22, 1979

[51] Int. Cl.³ .......................... H01B 7/08; A61N 1/14
[52] U.S. Cl. .................................................... 361/223
[58] Field of Search ................... 361/223, 224; 428/67, 428/94, 96, 175, 202, 247, 237, 408; 156/289

[56] References Cited

U.S. PATENT DOCUMENTS

| | | | |
|---|---|---|---|
| 2,785,344 | 3/1957 | Hines | 361/223 |
| 2,955,232 | 10/1960 | Price | 361/224 |
| 3,716,132 | 2/1973 | Lewyckyj | 428/247 |
| 3,832,598 | 8/1974 | Demmke et al. | 361/223 |

*Primary Examiner*—J. D. Miller
*Assistant Examiner*—L. C. Schroeder
*Attorney, Agent, or Firm*—Cruzan Alexander; Donald M. Sell; Robert W. Burns

[57] ABSTRACT

An electrically conductive strap to be secured to a shoe to ground static electricity accumulated on the body of the person wearing the shoe. The strap consists of an electrically conductive backing, a metallic strip that hooks over the upper edge of a shoe to secure one end of the strap, a pressure-sensitive adhesive coated over the backing and an open mesh scrim applied onto the adhesive which, prior to the application of pressure on the strap, has one surface extending above the adhesive to form a tack-free surface to permit ease of handling prior to use and positioning along the sides and across the bottom of the shoe. The strap adheres to the bottom of the shoe upon pressing the shoe against the floor. The scrim prevents the adhesive from adhering to the side of the shoe as no pressure is applied in this area. Additionally, the strap has a series of transverse rows of perforations so that segments of the strap can be removed to permit the strap to fit various sizes of shoes. Further, the need for a segmented liner is eliminated as the strap adheres to the shoe surface only in those areas where pressure is applied.

4 Claims, 7 Drawing Figures

GROUNDING STRAP

BACKGROUND OF THE INVENTION (1) Field of the Invention

This invention relates to a disposable grounding strap for shoes for the purpose of preventing the accumulation of static electricity on personnel who are engaged in vocations such as assembly or fabrication of electronic components, operation of computer systems, and in potentially hazardous environments where there is a possibility of explosive atmospheric conditions, for example, operating rooms utilizing flammable anaesthetics, the manufacture or distribution of flammable liquids or gasses, etc.

The strap is a narrow flexible conductive article with one end positioned to the upper edge of a wearer's shoe by means of an elongated metal strip and the opposite end secured by pressure-sensitive adhesive to the sole or heel of the wearer's shoe.

(2) Description of the Prior Art

There are numerous shoe grounding devices in the prior art. For example, W. C. Legge has a series of patents such as U.S. Pat. No. 2,933,651, issued Apr. 19, 1960 showing a strap which buckles to a wearer's leg and electrically connected to a grounding device strapped to a shoe; U.S. Pat. No. 3,379,932 issued Apr. 23, 1968 for a similar device which has means to adjust straps around the wearer's leg and shoe; and U.S. Pat. No. 3,775,509 issued Apr. 9, 1968 which shows a grounding device secured by straps to a shoe with grounding contact made to the floor by means of a conductive flexible tube. However, all of the Legge devices require manipulation of buckles or straps to one's shoe and leg and adjustment of wires which conduct static charges from the wearer's body to the grounding device.

U.S. Pat. No. 3,993,932 to Weigl issued Nov. 23, 1976 utilizes a grounding web integrally formed with a shoe sole.

In addition to various mechanically adjusted strapping devices for antistatic footwear, pressure-sensitive adhesives have been used to adhere the grounding strap to the bottom of a shoe and to assist in the connection of a free end of the strap to the ankle or lower leg of the wearer.

For example, U.S. Pat. No. 3,832,598 to Oehmke issued Aug. 27, 1974 illustrates a shoe strap consisting of a flexible conductive backing with a pressure-sensitive adhesive covered by a release liner. The adhesive adheres the strap to the bottom of the shoe upon removal of the liner. The free end of the strap is also secured by an adhesive on the wearer's ankle.

The patent to Hines U.S. Pat. No. 2,785,344 issued Mar. 12, 1957 also utilizes a pressure-sensitive adhesive. Here the grounding strap consists of two parts joined by a fastener 10 so that the lower portion of the strap which adheres to the heel of the shoe can be discarded or replaced. Both the lower and upper part of the strap are adhered by an adhesive which is coated onto a flexible backing to form the surface of the strap which interfaces with and adheres to the wearer's shoe.

One problem with adhesive grounding straps in the prior art is that they require the use and removal of protective liners. Once the liner is removed and the adhesive surface is exposed for positioning on the shoe, the tacky surface renders the strap difficult to handle and difficult to precisely position on the shoe heel or sole. Further if the strap and adhesive coated thereon extend up the sides of the shoe and/or are made in comparatively long lengths to fit a wide range of shoe sizes and shapes, the exposed adhesive may contact the sides of the shoe and possibly damage the shoe when the strap is removed.

SUMMARY OF THE INVENTION

This invention is directed to a grounding strap that is inexpensive and easy to fabricate, is free of a tacky adhesive surface during distribution and handling and at the time the strap is positioned under the wearer's shoe. Further, the strap can be easily adapted to shoes and boots of various sizes. The product is inexpensively fabricated in sheets or rolls with the individual straps die-cut therefrom as small, unobtrusive and easy to use antistatic footware. Because of their low cost and ease of manufacture, the straps are disposable, i.e. they can be worn during a normal working day and then discarded.

The strap comprises a polymeric conductive backing with a pressure-sensitive adhesive coated over the backing. The coating extends from one end of the strap along a substantial portion of its length although the opposite end is free of adhesive. An open mesh scrim is disposed on the adhesive coating, the upper surface of the scrim positioned above the exposed surface of the adhesive. The scrim serves as a shield over the adhesive during the time the strap material is stored after manufacture, cut into individual straps, distributed in the market and eventually placed in desired position on a shoe. The scrim prevents the tacky surface of the adhesive from adhering to other surfaces until the strap is in the exact selected position under the wearer's shoe. Once in selected position under the sole or heel of a shoe, pressure is applied to the backing (e.g., by pressing the shoe against the floor). The adhesive in the area where pressure is applied indents from the force of pressure up through the interstices formed in the scrim to contact the sole or heel of the shoe to secure the strap. The scrim covered adhesive portion of the strap that passes up the side of the shoe does not adhere because there is little or no pressure applied to these positions along the strap. It is therefore not necessary to remove a conventional paper release liner in segments along the part of the strap that adheres to the bottom of a shoe while leaving the liner intact on that part of the strap adjacent the sides of the shoe.

A series of rows of perforations are disposed transversely along the length of the strap so that segments may be torn off to permit the strap to be shortened to fit various sizes of shoes.

A flexible or malleable metallic strip is adhered to the end of the strap that is free of the adhesive. The purpose of the strip is to fold the strap over the upper edge of the shoe to secure the free end on the shoe and to provide opportunity for electrical contact between the strap and the wearer's foot or stocking.

The resistance of the strap is within parameters which permit substantially instant dissipation of static charges built up on the wearer's body but on the other hand reduce the possibility the strap will serve as a hazardous grounding path in event the wearer accidently contacts an electrical power source.

Detailed Description

Figure 1:
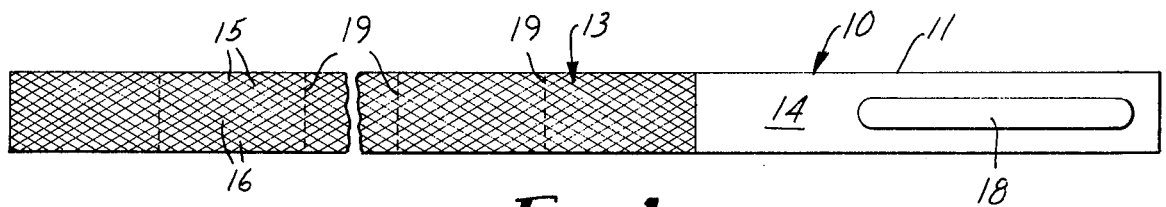
FIG. 1 is a top view of the strap partly broken away.

Referring to FIG. 1 the grounding strap 10 consists of an elongated structure approximately ½ inch (1.27 cm) wide and ranging in length from 6 to 22 inches (15.2 cm to 55.9 cm). The varying lengths permit the strap to be used with shoes and boots of different sizes and shapes.

A strap approximately 12 inches (30.5 cm) in length and ½ inch (1.27 cm) in width proved to be a satisfactory size for many applications.

Figure 2:
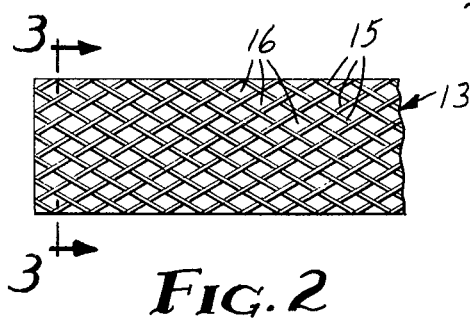
FIG. 2 is an enlarged top view of the strap showing the scrim disposed on the upper surface.
Figure 3:
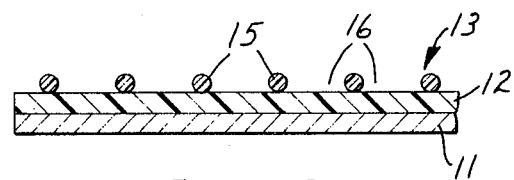
FIG. 3 is an enlarged cross-section along the lines and in the direction of the arrows 3—3 of FIG. 2.

As seen in FIGS. 2 and 3, strap 10 is a laminated structure consisting of a conductive film or backing 11, adhesive 12 and a reticulated web or scrim generally designated 13.

Backing 11 is preferably fabricated from ethylene vinyl acetate film loaded with carbon particles the latter rendering the backing conductive. However, other carbon loaded resins such as rubber, polyethylene, ultra high molecular weight polyolefin, epichlorohydrin rubber and vinyl perform satisfactorily as backing material.

When using ethylene vinyl acetate it was found that a copolymer of about 8% vinyl acetate and 92% polyethylene served satisfactorily. To provide the backing with adequate electrically conductive characteristics, conductive carbon particles in the range of 10–40% by weight were added to the ethylene vinyl acetate copolymer. The preferred percentage of carbon particles was found to be about 25%.

Proper selection of the conductive properties for the backing is essential to provide (1) adequate and practically instantaneous discharge of static charges that build up on the wearer's body and (2) at the same time provide adequate electrical insulation so that the strap does not become a hazardous ground short in event the wearer should accidently contact electrical power sources. In addition the backing must have suitable characteristics of elasticity and flexibility in order to properly coact with the adhesive 12 and scrim 13 to provide adequate adhesion to the sole or heel of one's shoe. A film having a caliper of 6–8 mils (0.015 cm to 0.02 cm) and an elastic modulus of 15,000 pounds per square inch (1056 Kg/cm$^2$) via ASTM No. D882 was found to perform satisfactorily. The caliper, elasticity and flexibility of the backing should correlate closely with the characteristics of the adhesive and scrim to provide optimum adhesion.

The strap material may be fabricated in large rolls or sheets and individual straps die cut therefrom in desired sizes. This manner of fabrication permits the pressure-sensitive adhesive 12 to be coated on the backing 11 by any well-known process. Then utilizing ethylene vinyl acetate as the backing 11, it is preferred to apply a primer on the backing before coating on the adhesive. A primer consisting of 5% by weight of chlorinated polypropylene resin dissolved in tolulene worked satisfactorly.

Well-known copolymers such as those consisting of 95.5% iso octyl acrylate and 4.5% acrylic acid function well as an adhesive. For most applications, the adhesive 12 can be coated at a weight of 10 grains /4"×6" (0.004 grams/cm$^2$). However the weight and thickness of the adhesive varies with the characteristics of backing 11 and scrim 13 as explained in more detail below.

Figure 7:
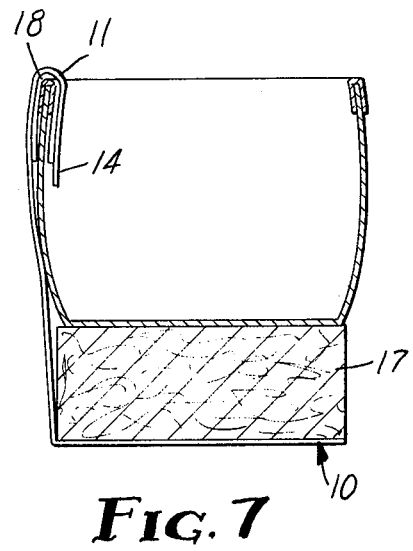
FIG. 7 is a cross-section of a shoe showing the strap secured to a shoe.

An adhesive free portion 14 is formed at one end of strap 10 so that the strap can be folded over the upper edge of the wearer's shoe as seen in FIG. 7. When fabricating the straps from sheets or rolls of material, it is preferred to die cut the individual straps transversely to the sheet or roll. In such case adhesive 12 is applied in strips along the linear length of the sheet or roll providing for the formation of the adhesive-free portions 14 between the strips.

As shown in FIGS. 2 and 3, an open mesh scrim 13 is suitably secured to the exposed and tacky surface of that portion of backing 11 which is coated with pressure-sensitive adhesive 12. Inasmuch as the upper surface of the scrim is disposed in a plane above the plane of the surface of the adhesive, the scrim serves as a reticulum or shield to prevent the tacky surface of adhesive 12 from sticking to surfaces (including the wearer's fingers) prior to the time the strap is placed in desired position under the user's shoe. With the scrim forming a tack free surface, the strap material can be easily rolled, stored, distributed, handled and finally positioned in exact position without premature sticking or other disadvantageous situations that occur in handling the customary tacky surface of adhesive tapes or without subsequent adhesion to the delicate and damageable surfaces of the sides of a shoe.

As visualized from viewing FIGS. 2 and 3, the scrim 13 comprises a series of strands 15 to form a fine mesh or netting with interstices 16. Strands 15 consist of two nylon filaments twisted together to form the single strand. A nylon scrim having approximately 16 interstices per inch (2.54 cm) in linear length and a caliper of 3 mils (0.008 cm) proved satisfactory for most applications.

As indicated above, prior to securing strap 10 onto a heel 17 of a shoe, the scrim provides a shield over the surface of adhesive 12. As visualized when viewing FIGS. 4 and 7, once the strap has been placed in desired position under heel 17, the shoe heel is pressed onto a hard surface (as by pressing on the floor with one's heel). The pressure of heel 17 on strands 15 of scrim 13 causes adhesive 12 (which, of course, is flexible) along with flexible backing 11 to deform and indent so that the adhesive is forced up into the interstices 16 formed in scrim 13. In the indented position of FIG. 4 the adhesive extending up through the interstices 16 contacts and adheres to the surface of heel 17. The indentations of adhesive 12 and backing 11 are substantially in registry with the position and size of interstices 16.

Figure 4:
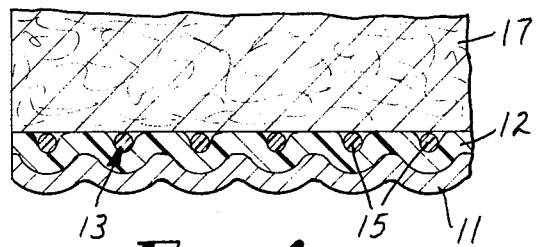
FIG. 4 is an enlarged cross-sectional view of FIG. 3 but showing the strap adhered to the heel of a shoe.
Figure 5:
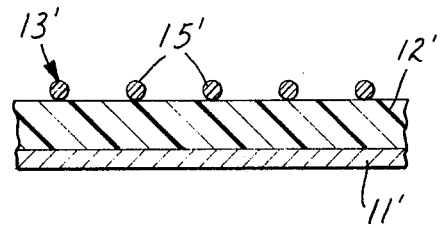
FIG. 5 is an enlarged cross-section of a modified form of the invention.
Figure 6:
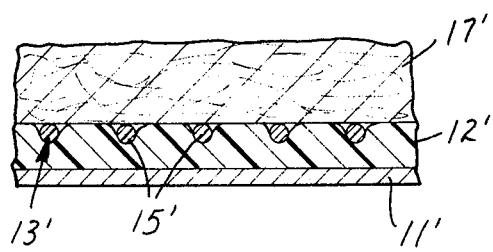
FIG. 6 is an enlarged cross-section of the FIG. 5 modification showing the strap secured to the heel of a shoe.

A modified form of the invention which is indicated in FIGS. 5 and 6, utilizes a backing 11' which is not as flexible as the backing 11 in the FIG. 3 and 4 embodiment. Furthermore, the adhesive 12' has a caliper equal to or greater than the caliper of scrim 13' [the preferred caliper of the adhesive 12' being about 5 mils (0.013 cm)]. The adhesive usually consists of soft waxy material (e.g. a standard pressure-sensitive adhesive with a micro crystalline wax) to form a comparatively soft matrix. The scrim 13' is applied as previously described.

Similar to the embodiments of FIGS. 3 and 4, the upper surface of scrim 13' is disposed in a plane above the surface of the adhesive 12' and forms the reticulated shield. Upon applying pressure to the scrim 13' (such as pressing down onto the scrim by means of a shoe heel 17') the scrim in this embodiment "sinks" or is forced into the soft layer of adhesive. In such case, the backing 11' does not tend to indent in registry with the interstices of the scrim but remains substantially planar. Thus, the backing 11' can exhibit substantially less flexible characteristics than the backing in the FIGS. 3 and 4 embodiment. This gives a somewhat wider choice of conductive backing materials.

Since the strap material of either embodiment can be economically fabricated and the straps easily die cut from the material, the straps are comparatively inexpensive and thus can be marketed as disposable products, (i.e. the wearer can use them during a normal day's activity and then discard them).

In order to achieve a disposable strap that will successfully adhere to the wearer's shoe during a normal day of activity, attention must be given to the adhering capabilities of the strap. In this respect it is important that the various characteristics and parameters of the backing, adhesive and scrim be closely correlated. For example, the caliper, flexibility and elastic modulus of the backing should correlate with the sizes of the strands 15, interstices 16 and the caliper of the scrim 13. These characteristics in turn must correlate with the dimensions and adhering properties of adhesive 12 in order that the adhesive and backing, upon pressure, properly indent in registry with the interstices 16 of scrim 13 and the surface of the adhesive extends up through the interstices to adhere to heel 16.

Alternately in the FIGS. 5 and 6 modification, the adhesive should preferably be softer so that the scrim will easily "sink" into the adhesive upon the application of pressure. Upon such application, the adhesive will appear through the interstices 16' to adhere to heel 17'.

The adhering capabilities of strap material fabricated in various dimensions were determined by pressing a 1"×1½" (2.54 cm×3.81 cm) piece of strap material (based on the FIGS. 3 and 4 embodiment) against a rubber surface simulating a shoe heel at a pressure of 33 pounds per sq. in. (2.3 Kg/cm$^2$). The characteristics of the various samples and the peel strength for each sample are shown in Table I. The adhering capabilities of each Table I sample are expressed in terms of peel strength which was determined by means of an Instron testing device. The peel strength was based on the force required to peel the sample material off the rubber surface at a 90° angle and at a rate of 5"/min (12.7 cm/min).

TABLE I

| Sample Number | Backing Caliper (centimeters) | Adhesive Weight (Grams/cm$^2$) | Scrim Holes Per Linear CM | Peel Strength (grams) |
|---|---|---|---|---|
| 1 | .02 | .0006 | 16 | 72.6 |
| 2 | .02 | .0006 | 20 | 40.9 |
| 3 | .02 | .004 | 16 | 172.5 |
| 4 | .02 | .004 | 20 | 113.5 |
| 5 | .015 | .004 | 16 | 177.1 |
| 6 | .015 | .004 | 20 | 158.9 |

In addition to the above tests, a series of grounding straps 10 based on the composition of samples 1-6 above were used during a normal day's work by personnel wearing the straps under actual working conditions. It was found that samples 1 and 2 tended to loosen during the day. Samples 3-6 however exhibited good adhering characteristics under actual conditions throughout the work day.

Thus, it is seen that various combinations of backing caliper, adhesive weight, caliper and size of scrim interstices, etc. can be varied to produce straps with satisfactory adhering capabilities needed for a disposable item of this type.

Referring to FIGS. 1 and 7, a malleable metallic strip 18 (preferably made of aluminum with both ends rounded) is secured to the strap in adhesive free portion 14. Strip 18 may be adhered to the backing 11 by the same pressure-sensitive adhesive that is used as adhesive layer 12. The adhesive is coated directly onto one side of strip 18 and adhered to backing 11. Strip 18 may be substantially smaller than the adhesive free portion 14, the preferred smaller size of the strip being 1¾"×3/16"×0.021" (4.4 cm×0.48 cm×0.05 cm). Strip 18 serves as a malleable piece that can be easily folded on itself to form a hook that engages the upper edge of the shoe to anchor the upper end of strap 10 thereto. Strip 18 also ensures that conductive backing 11 of strap 10 makes physical and electrical contact with the wearer's foot or stocking.

If desired the adhesive free portion 14 of strap 10 can be extended beyond the outer end of strip 18 so that portion 14 of the conductive backing material extends well into the wearer's shoe to make better electrical contact with the wearer's foot or stocking.

Strap 10 has a series of rows of perforations 19 disposed transversely across the strap so that segments can be torn off by means of the perforations to fit the wearer's shoe as visualized from FIGS. 1 and 7. The rows of perforations may be spaced about ½ inch (1.27 cm) to 2 inches (5.1 cm) apart, the preferred distance being about 1 inch (2.54 cm). Sufficient perforations are made in each row to provide a breaking strength [pounds (grams) of force needed to separate the strap at the perforations] in the range of 5 to 15 lbs. (2.3 Kg to 6.8 Kg), the preferred strength being about 9 lbs. (4.1 Kg).

It is important that the electrical discharge characteristics of the strap be confined within desired parameters so that it will properly and quickly dissipate static charges built up on the wearer's body but will not endanger the wearer in case of accidental contact with electrical power sources. For example, and assuming good electrical contact with the wearer's ankle and foot and that the wearer is standing on a good electrical ground (flooring, matting, carpeting, etc. having good conductive characteristics), the maximum level of strap resistance, (as installed on a wearer's shoe) should render the strap capable of dissipating a static charge on the wearer's body from 5000 volts to 500 volts in a one second interval. Minimum resistance of the strap (as installed on a wearer's shoe) should be within parameters that will prevent the strap from serving as a harmful conductive path in the event the wearer touches an electric power source. A properly installed strap which permits a 5 milliamps current flow through the strap in event the wearer should contact a power source of 110 volts was found to be within safe minimum resistance parameters.

Substantially instantaneous dissipation of a static charge to a ground such as electrical grounding mats or flooring is essential. In the event a static charge is built up on the wearer's body as he approaches static sensitive equipment (e.g., solid state electronic assembly stations or computer terminals), the charge should be quickly dissipated so that the wearer is static-free upon actual contact with the equipment. To provide substantially instantaneous dissipation the strap should be capable of dissipating the charge in one second or less.

Table II shows the electrical discharge characteristics of several samples of grounding strap materials (of the FIG. 3 and 4 embodiment) cut into six inch lengths. A capacitor of $200 \times 10^{-12}$ farads (substantially equal to the electrical capacitance of the human body) was charged to 5000 volts and then discharged via the strap samples to 500 volts.

TABLE II

| SAMPLE NUMBER | RESISTANCE (IN OHMS) | DISCHARGE TIME (Seconds) 5000 to 500 VOLTS |
|---|---|---|
| 1 | $2 \times 10^9$ | 1 |
| 2 | $1 \times 10^9$ | 0.5 |
| 3 | $5 \times 10^8$ | 0.25 |
| 4 | $2.2 \times 10^4$ | $1 \times 10^{-5}$ |

Straps within these ranges of resistance quickly dissipate static charges but do not pose significant electrical hazards to the wearer.

In addition to being produced at low cost, the straps are easy to apply to one's shoe. As visualized in FIG. 7, strip 18 is bent into a hook shape to engage the upper edge of the shoe. Adhesive free portion 14 contacts the foot or stocking along the inside surface of the shoe. The adhesive coated portion of the strap is drawn down alongside the shoe and underneath and across the heel or sole. Any excess material extending beyond the heel is removed by means of the rows of perforations. Once positioned with the fingers, pressure is applied to the sole or heel causing adhesive 12 to extend up through interstices 16 and adhere to the bottom of the shoe. Since pressure is not applied to the side of the shoe, scrim 13 prevents the adhesive from sticking to and possibly damaging the side of the shoe.

What is claimed is:

1. A grounding strap adhesively attached to a shoe comprising:
    (a) a flexible conductive backing,
    (b) a pressure-sensitive adhesive coating on one surface of the backing extending from one end of the backing but terminating short of the opposite end so that the backing extends beyond the adhesive,
    (c) an open mesh scrim, the scrim forming a series of interstices, one surface of the scrim secured to the adhesive and the opposite surface extending above the plane of the surface of the adhesive forming a shield to provide a tack-free surface over the adhesive and upon pressure applied to said backing, the backing indents forcing the adhesive through the interstices for adhesive contact to a surface of said shoe,
    (d) flexible metallic means secured to the backing at the end of the backing extending beyond the adhesive for fastening one end of the strap to the upper edge of a shoe, and
    (e) rows of perforations transversely disposed at longitudinally spaced intervals along the adhesive coated surface of the backing, the perforations extending through the backing and adhesive for removing segments of the strap to correlate the strap length to the dimensions of a shoe.

2. A grounding strap according to claim 1 wherein said rows of perforations are spaced apart from each other in the range of 1.27 cm to 5.1 cm, the lateral spacing of the individual perforations from each other in a given row providing a breaking strength in the range of 2.3 Kg to 6.8 Kg.

3. A grounding strap for adhering to the bottom of a shoe comprising:
    (1) a flexible electrically conductive polymeric backing,
    (2) an adhesive coating onto one side of said backing, and
    (3) an open mesh scrim disposed above the surface of said adhesive to form a shield thereover,
said grounding strap being characterized in that:
    (A) upon pressure supplied to said backing or scrim, adhesive is forced through the interstices of said scrim for adhesive contact with said shoe, the peel strength resulting from said contact of the adhesive with the bottom of the shoe being in the range of 113.5 to 177.1 grams when the strap is applied to the shoe bottom at a pressure of 2.3 Kg/cm$^2$.

4. A grounding strap for adhering to the bottom of a shoe comprising:
    (1) a flexible electrically conductive polymeric backing having a maximum caliper of 0.02 cm,
    (2) a pressure sensitive adhesive coated onto one side of said backing, and
    (3) a scrim having about 6 to 8 interstices per cm and a caliper of about 0.008 cm disposed over said adhesive to form a shield thereover,
said grounding strap being characterized in that:
    (A) the polymeric backing has an elastic modulus of about 1056 Kg/cm$^2$ as measured by ASTM No. D882,
    (B) the adhesive has a weight of about 0.004 gm/cm$^2$,
    (C) the interstices provided by said scrim are of a size sufficient to permit the backing to indent and the adhesive to extend therethrough and adhere to the bottom of said shoe upon application of pressure to said scrim or backing, and
    (D) said strap has an electrical resistance in the range of $2.2 \times 10^4$ to $2 \times 10^9$ ohms and a peel strength in the range of 113.5 to 177.1 grams at the interface of the bottom of said shoe and the adhesive when the adhesive is extended through said interstices and the strap is applied to said shoe bottom at a pressure of 2.3 Kg/cm$^2$.

* * * * *